US012625472B2

(12) United States Patent (10) Patent No.: US 12,625,472 B2

Mobley (45) Date of Patent: May 12, 2026

(54) TACTICAL WATCH

(71) Applicant: Jaylan Mobley, Huntington, WV (US)

(72) Inventor: Jaylan Mobley, Huntington, WV (US)

( * ) Notice: Subject to any disclaimer, the term of this patent is extended or adjusted under 35 U.S.C. 154(b) by 304 days.

(21) Appl. No.: 18/197,777

(22) Filed: May 16, 2023

(65) Prior Publication Data

US 2024/0385574 A1 Nov. 21, 2024

(51) Int. Cl.
| | |
|---|---|
| *G04B 21/00* | (2006.01) |
| *A61B 5/00* | (2006.01) |
| *A61B 5/11* | (2006.01) |
| *G04B 37/08* | (2006.01) |
| *G04G 9/00* | (2006.01) |
| *G04G 21/02* | (2010.01) |
| *G04G 21/04* | (2013.01) |
| *G04G 21/08* | (2010.01) |
| *G06F 3/041* | (2006.01) |
| *G06F 3/0482* | (2013.01) |

(52) U.S. Cl.
CPC ............ *G04G 9/007* (2013.01); *A61B 5/1126* (2013.01); *A61B 5/681* (2013.01); *A61B 5/743* (2013.01); *G04B 37/08* (2013.01); *G04G 21/025* (2013.01); *G04G 21/04* (2013.01); *G04G 21/08* (2013.01); *G06F 3/041* (2013.01); *G06F 3/0482* (2013.01); *A61B 2562/0219* (2013.01); *A61B 2562/028* (2013.01)

(58) Field of Classification Search
CPC ........ G04G 9/007; G04G 21/00; G04G 21/08; G04G 21/025; G04B 37/08; A61B 5/681; A61B 5/1126
See application file for complete search history.

(56) References Cited

U.S. PATENT DOCUMENTS

| | | | | |
|---|---|---|---|---|
| 3,293,846 A | * | 12/1966 | Pauli ................. | G04B 37/1486 |
| | | | | 368/282 |
| 5,479,381 A | * | 12/1995 | Goldenberg ....... | G04B 45/0084 |
| | | | | 224/175 |
| D448,679 S | * | 10/2001 | Muller .......................... | D10/38 |
| D452,169 S | * | 12/2001 | Syoubayashi ................. | D10/38 |
| 6,443,614 B1 | * | 9/2002 | Read ................... | G04G 9/0064 |
| | | | | 368/187 |
| 6,463,011 B1 | * | 10/2002 | Christen ............... | G04C 3/005 |
| | | | | 368/69 |
| 6,619,835 B2 | * | 9/2003 | Kita ..................... | A44C 5/0015 |
| | | | | 368/282 |
| 6,779,917 B1 | * | 8/2004 | Chappuis ........... | G04B 37/0083 |
| | | | | 368/282 |
| D546,725 S | * | 7/2007 | Goto ........................... | D10/128 |

(Continued)

FOREIGN PATENT DOCUMENTS

WO 2022155014 7/2022

*Primary Examiner* — Sean Kayes
(74) *Attorney, Agent, or Firm* — Kyle A. Fletcher, Esq.

(57) ABSTRACT

The tactical watch includes a dorsal case, a volar case, a plurality of buttons, one or more sensors, and a band. The tactical watch may be a multi-purpose time-keeping device adapted to be worn on a wrist. The band may encircle the wrist with the dorsal case positioned on a dorsal side of the wrist and the volar case positioned on a volar side of the wrist. An outward facing display on the dorsal case and an inward facing display on the volar case may display the time, biometric data, and other information. The plurality of buttons may be adapted for a user to press in order to control features of the tactical watch.

18 Claims, 5 Drawing Sheets

(56) References Cited

U.S. PATENT DOCUMENTS

| | | | |
|---|---|---|---|
| 9,152,129 B2 * | 10/2015 | Modaragamage | ....... G04G 9/00 |
| 9,497,307 B2 | 11/2016 | Jiang | |
| 9,671,762 B2 | 6/2017 | Chen | |
| 9,744,943 B1 * | 8/2017 | Hiatt | .................. G07C 9/00182 |
| 10,318,958 B2 | 6/2019 | Kim | |
| 10,688,962 B2 * | 6/2020 | House | .................... G04B 47/00 |
| D895,613 S | 9/2020 | Kozlovskaya | |
| 11,062,584 B1 | 7/2021 | Magaletta | |
| D931,276 S | 9/2021 | Yi | |
| 11,368,043 B1 | 6/2022 | Gamble | |
| D962,932 S | 9/2022 | He | |
| 2003/0019894 A1 * | 1/2003 | Caldana | ................. H04B 1/385 |
| | | | 224/267 |
| 2004/0100872 A1 * | 5/2004 | Nobs | ...................... G04G 21/00 |
| | | | 368/82 |
| 2006/0178055 A1 * | 8/2006 | Robin | .................. H01R 13/521 |
| | | | 439/660 |
| 2007/0279852 A1 * | 12/2007 | Daniel | ................... H04B 1/385 |
| | | | 361/728 |
| 2008/0043575 A1 * | 2/2008 | Fasciano | .............. G04G 9/0076 |
| | | | 368/13 |
| 2008/0049562 A1 * | 2/2008 | Andren | ................ G04B 19/283 |
| | | | 368/295 |
| 2008/0318636 A1 * | 12/2008 | Kim | .................. H04M 1/72469 |
| | | | 455/566 |
| 2015/0124567 A1 * | 5/2015 | Liao | ....................... G04G 21/04 |
| | | | 368/282 |
| 2016/0085397 A1 | 3/2016 | Jain | |
| 2018/0294554 A1 * | 10/2018 | Xu | ......................... G04G 17/04 |
| 2019/0196411 A1 | 6/2019 | Yuen | |
| 2021/0052221 A1 | 2/2021 | Selvam | |
| 2021/0401331 A1 | 12/2021 | Flores | |

* cited by examiner

TACTICAL WATCH

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of timing-keeping devices, more specifically, a tactical watch.

SUMMARY OF INVENTION

The tactical watch comprises a dorsal case, a volar case, a plurality of buttons, one or more sensors, and a band. The tactical watch may be a multi-purpose time-keeping device adapted to be worn on a wrist. The band may encircle the wrist with the dorsal case positioned on a dorsal side of the wrist and the volar case positioned on a volar side of the wrist. An outward facing display on the dorsal case and an inward facing display on the volar case may display the time, biometric data, and other information. The plurality of buttons may be adapted for a user to press in order to control features of the tactical watch. The one or more sensors may be adapted to monitor the user and/or the environment surrounding the tactical watch.

An object of the invention is to provide a time-keeping device comprising a dorsal case worn over the dorsal side of the wrist, a volar case worn over the volar side of the wrist, and a band that surrounds the wrist and couples to the dorsal case and the volar case.

Another object of the invention is to provide an outward facing display on the dorsal case and an inward facing display on the volar case.

A further object of the invention is to provide a plurality of buttons that are easily accessible even by a gloved hand for navigating menus of the invention.

Yet another object of the invention is to provide a biometric contact sensor, motion sensor, and GPS receiver for monitoring biometric data and movement of the user.

These together with additional objects, features and advantages of the tactical watch will be readily apparent to those of ordinary skill in the art upon reading the following detailed description of the presently preferred, but nonetheless illustrative, embodiments when taken in conjunction with the accompanying drawings.

In this respect, before explaining the current embodiments of the tactical watch in detail, it is to be understood that the tactical watch is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the tactical watch.

It is therefore important that the claims be regarded as including such equivalent construction insofar as they do not depart from the spirit and scope of the tactical watch. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
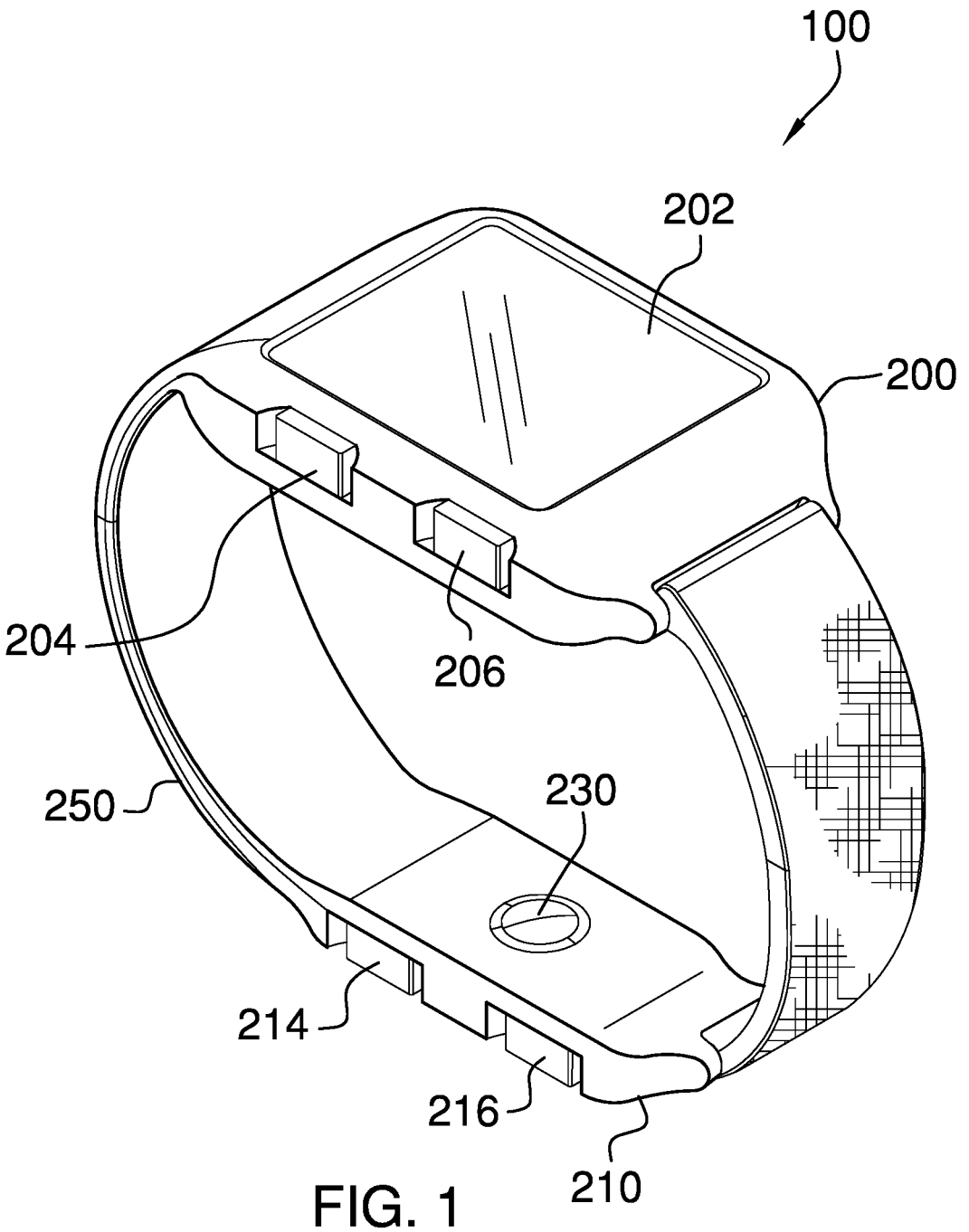
FIG. 1 is an isometric view of an embodiment of the disclosure.
Figures 2, 3:
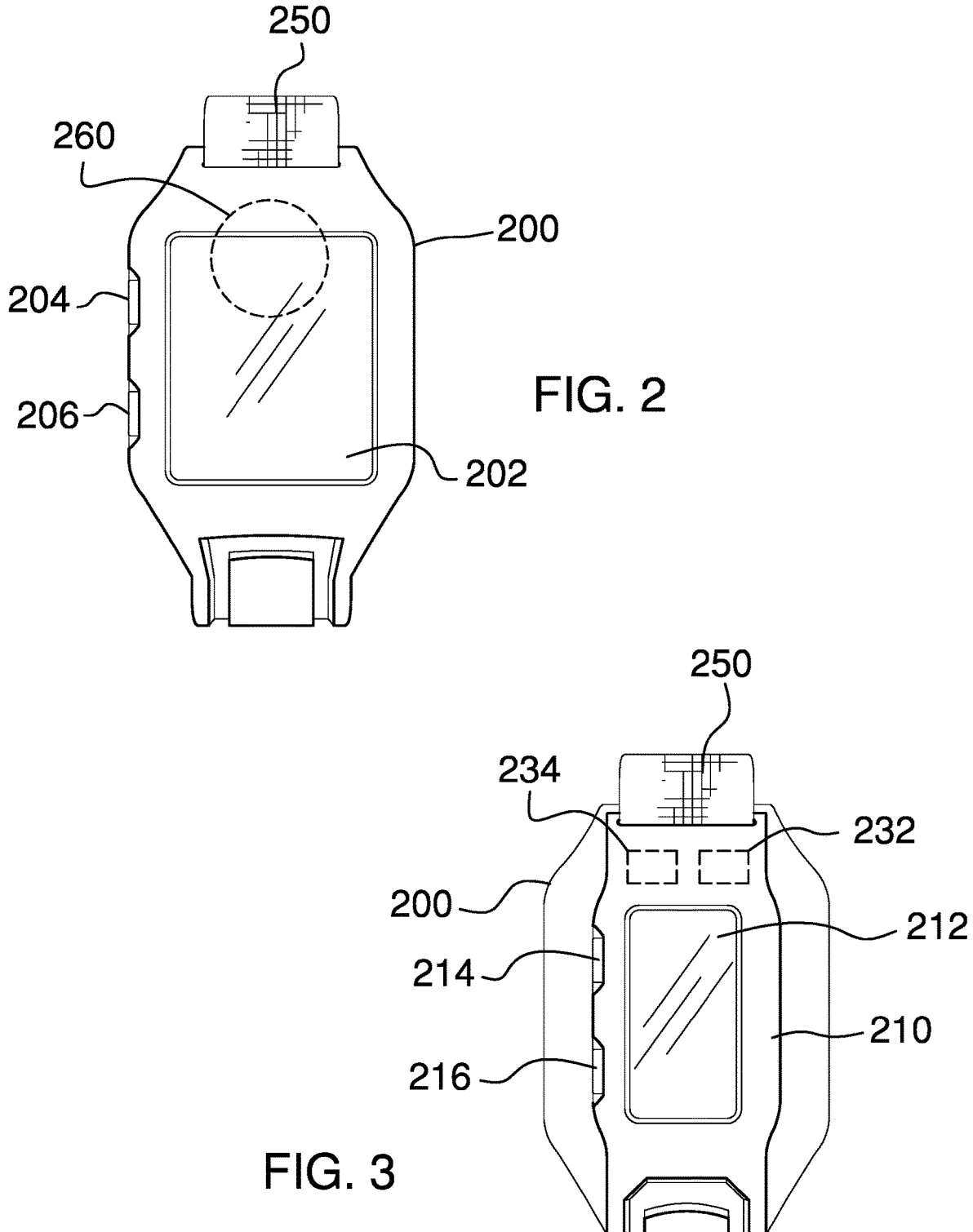
FIG. 2 is a dorsal view of an embodiment of the disclosure.
FIG. 3 is a volar view of an embodiment of the disclosure.
Figure 4:
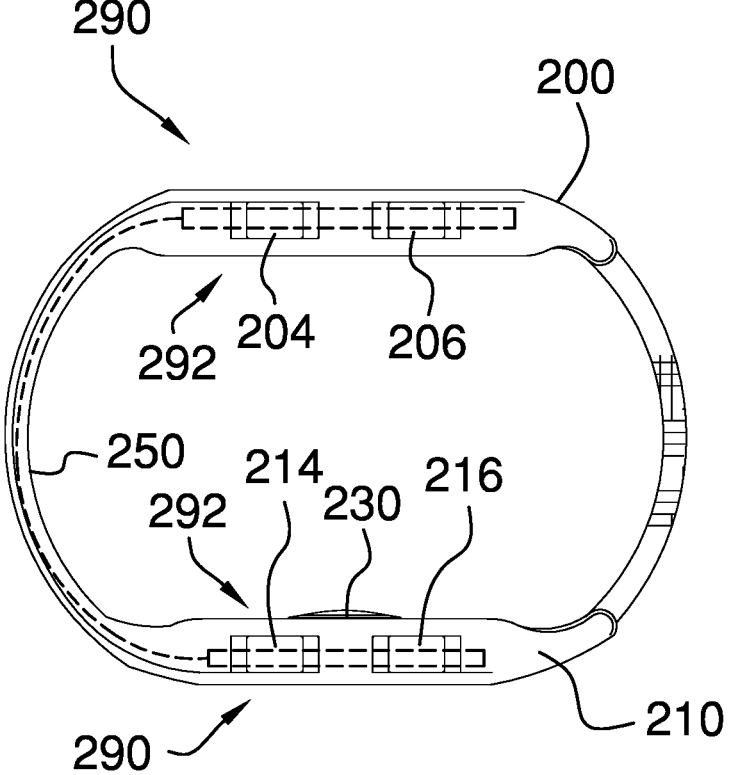
FIG. 4 is a side view of an embodiment of the disclosure.
Figure 5:
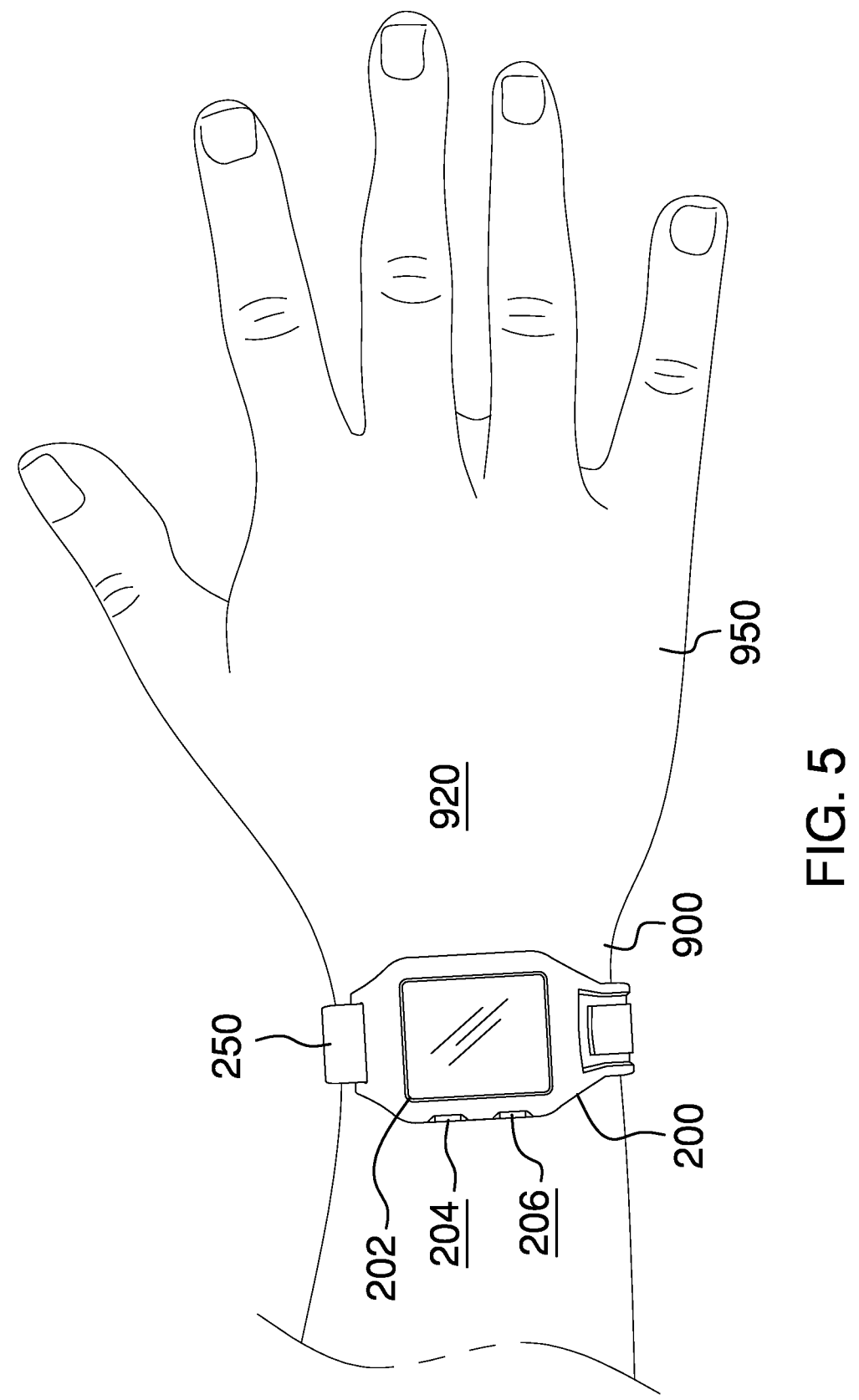
FIG. 5 is an in-use view of an embodiment of the disclosure, illustrating the outward facing display.
Figure 6:
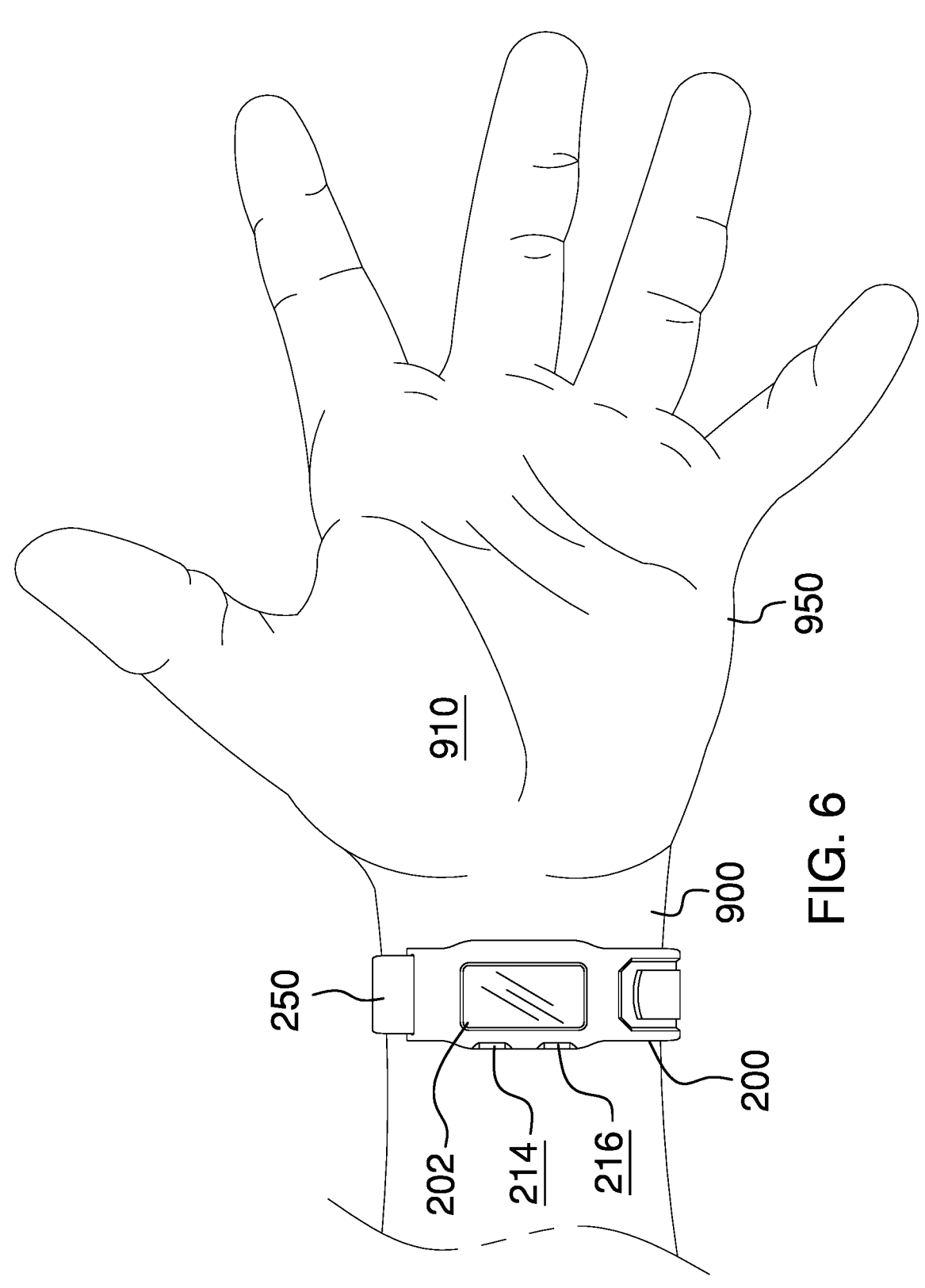
FIG. 6 is an in-use view of an embodiment of the disclosure, illustrating the inward facing display.

Detailed reference will now be made to a first potential embodiment of the disclosure, which is illustrated in FIGS. 1 through 6.

The tactical watch 100 (hereinafter invention) comprises a dorsal case 200, a volar case 210, a plurality of buttons, one or more sensors, and a band 250. The invention 100 may be a multi-purpose time-keeping device adapted to be worn on a wrist 900. The band 250 may encircle the wrist 900 with the dorsal case 200 positioned on a dorsal side 920 of the wrist 900 and the volar case 210 positioned on a volar side 910 of the wrist 900. An outward facing display 202 on the dorsal case 200 and an inward facing display 212 on the volar case 210 may display the time, biometric data, and other information. The plurality of buttons may be adapted for a user 950 to press in order to control features of the invention 100. The one or more sensors may be adapted to monitor the user 950 and/or the environment surrounding the invention 100.

The dorsal case 200 may be coupled to the band 250 and may be adapted to be worn on the dorsal side 920 of the wrist 900. The volar case 210 may be coupled to the band 250 and may be adapted to be worn on the volar side 910 of the wrist 900. The volar case 210 may be positioned on the band 250 opposite the dorsal case 200. The dorsal case 200 and the volar case 210 may each comprise an obverse face 290 and a reverse face 292 with the reverse face 292 adapted to contact the wrist 900 and the obverse face 290 opposite the reverse face 292. The band 250 may be elastic such that the band 250 may stretch for donning and removing. The invention 100 may comprise electrical connections between the dorsal case 200 and the volar case 210 that are hidden within the band 250. In some embodiments, the dorsal case 200, the volar case 210, or both may comprise a rubberized coating to absorb mechanical shock incurred by dropping the invention 100. The dorsal case 200 may comprise the outward facing display 202 located on the obverse face 290 of the dorsal case 200 and the volar case 210 may comprise the inward facing display 212 located on the obverse face 290 of the volar case 210. The outward facing display 202 may be adapted to be viewed by lifting a user's forearm. The inward facing display 212 may be adapted to be viewed by rotating the user's forearm by 180 degrees while viewing the outward facing display 202.

The plurality of buttons may comprise a first dorsal button 204, a second dorsal button 206, a first volar button 214, and a second volar button 216. The first dorsal button 204 and the second dorsal button 206 may be located on the dorsal case 200. The first dorsal button 204 and the second dorsal button 206 may be over-sized buttons that may be positioned at a corner of the dorsal case 200 for improved accessibility by a gloved hand. Specifically, the first dorsal button 204 and the second dorsal button 206 may be located where a side wall of the dorsal case 200 meets the obverse face 290 of the dorsal case 200. The first volar button 214 and the second volar button 216 may be located on the volar case 210. The first volar button 214 and the second volar button 216 may be over-sized buttons that may be positioned at a corner of the volar case 210 for improved accessibility by a gloved hand. Specifically, the first volar button 214 and the second volar button 216 may be located where a side wall of the volar case 210 meets the obverse face 290 of the volar case 210.

In some embodiments, the plurality of buttons may all be located on the same side of the invention 100 with the intent that the invention 100 is worn to position the plurality of buttons on the side opposite a user's hand.

The plurality of buttons may comprise at least one button designated as an UP button for navigating menus presented on the outward facing display 202, the inward facing display 212, or both. The plurality of buttons may comprise at least one button designated as a DOWN button for navigating menus presented on the outward facing display 202, the inward facing display 212, or both. The plurality of buttons may comprise at least one button designated as a SELECT/ENTER button for making selections from menus presented on the outward facing display 202, the inward facing display 212, or both.

The one or more sensors may be adapted to monitor the user 950 and/or the environment surrounding the invention 100. As a non-limiting example, the one or more sensors may comprise a biometric contact sensor 230. The biometric contact sensor 230 may be located on the reverse face 292 of the dorsal case 200, on the reverse face 292 of the volar case 210, or both. The biometric contact sensor 230 may be adapted to contact the wrist 900. The biometric contact sensor 230 may measure body temperature, pulse rate, blood oxygen level, blood pressure, or any combination thereof.

As a non-limiting example, the one or more sensors may comprise a motion sensor 232. The motion sensor 232 may be located within the dorsal case 200, within the volar case 210, or both. The motion sensor 232 may measure acceleration of the invention 100 within three-dimensional space. As a non-limiting example, the motion sensor 232 may utilize one or more MEMS 2 accelerometers.

In some embodiments, the invention 100 may comprise a GPS receiver 234 for determining the geographical location of the invention 100 and the current time.

The outward facing display 202, the inward facing display 212, or both may be touch sensitive such that the outward facing display 202 and/or the inward facing display 212 are adapted to accept input from the user 950.

A display selected from the outward facing display 202 and the inward facing display 212 may comprise features to reduce visibility of the invention 100 to adversaries. As non-limiting examples, the display may comprise a black background and a backlight having reduced visibility such as a red backlight.

The invention 100 may be adapted to present any or all of the following to the user 950 utilizing the outward facing display 202, the inward facing display 212, or both: a time and date, a GPS location comprising a longitude, a latitude, an elevation, or any combination thereof, a blood pressure measurement, a calories burned estimate, a body temperature measurement, and a pulse rate measurement.

The display may present one or more menus for changing settings of the invention 100. Navigation and selection of the settings may be performed using touchscreen displays.

The invention 100 may comprise a battery 260. The battery 260 may comprise one or more energy-storage devices. The battery 260 may be a source of electrical energy to operate the outward facing display 202, the inward facing display 212, the touchscreen displays, the backlight, the GPS receiver 234, and the one or more sensors. The battery 260 may be rechargeable and/or replaceable.

The dorsal case 200, the volar case 210, and the band 250 may be waterproof such that the invention 100 is unharmed by sweat or submersion in water.

In use, a user 950 may don the invention 100 by stretching the band 250 and sliding the band 250 onto the wrist 900 with the dorsal case 200 over the dorsal side 920 of the wrist 900 and the volar case 210 over the volar side 910 of the wrist 900.

The user 950 may interact with the invention 100 using the plurality of buttons and the touchscreen displays to navigate menus and adjust the settings. The biometric contact sensor 230 may measure biometric parameters of the user 950. The motion sensor 232 may monitor and track movements made by the user 950. The GPS receiver 234 may determine the geographical location and time. The outward facing display 202, the inward facing display 212, or both may display the time and date, the longitude, the latitude, the elevation, the blood pressure measurement, the calories burned estimate, the body temperature measurement, the pulse rate measurement, or any combination thereof.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

As used herein, "accelerometer" may refer to a device for measuring proper acceleration. An accelerometer may detect the magnitude and direction of proper acceleration along one or multiple axes and may be able to detect orientation.

Throughout this document the terms "battery", "battery pack", and "batteries" may be used interchangeably to refer to one or more wet or dry cells or batteries of cells in which chemical energy is converted into electricity and used as a source of DC power. References to recharging or replacing batteries may refer to recharging or replacing individual cells, individual batteries of cells, or a package of multiple battery cells as is appropriate for any given battery technology that may be used. The battery may require electrical contacts which may not be illustrated in the figures.

As used herein, the words "couple", "couples", "coupled" or "coupling", may refer to connecting, either directly or indirectly, and does not necessarily imply a mechanical connection.

As used herein, "dorsal" may refer to the upper or back side of a human, animal, plant or organ and "ventral" may refer to the lower or front side of the human, animal, plant, or organ. As applied to a hand, "dorsal" may refer to the back of the hand and "palmer" or "volar" may refer to the palm side of the hand.

As used in this disclosure, "elastic" may refer to a material or object that deforms when a force is applied to stretch or compress the material and that returns to its relaxed shape after the force is removed. A material that exhibits these qualities is also referred to as an elastomeric material.

As used herein, "GPS" may refer to a device that uses signals received from a system of navigational satellites to determine the position of the device. GPS is an acronym for Global Positioning System.

As used in this disclosure, a "sensor" may be a device that quantitatively measures a physical stimulus.

As used in this disclosure, a "touchscreen" may be an interface that allows a user to interface with a logical device by touching the image bearing surface of a display.

As used herein, the word "waterproof" may refer to an object that is not harmed when being exposed to water, including total submersion for a period of time. When used as a verb, "waterproof" may refer to taking steps to make an object waterproof. Non-limiting examples of such steps may include applying special coatings or using gaskets to seal seams and entry points of an enclosure.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A tactical watch comprising:
a dorsal case, a volar case, and a band;
wherein the tactical watch is a multi-purpose time-keeping device adapted to be worn on a wrist;
wherein the band encircles the wrist with the dorsal case positioned on a dorsal side of the wrist and the volar case positioned on a volar side of the wrist;
wherein an outward facing display on the dorsal case and an inward facing display on the volar case display the time, biometric data, and other information;
wherein a plurality of buttons comprise a first dorsal button, a second dorsal button, a first volar button, and a second volar button;
wherein the first dorsal button and the second dorsal button are located on the dorsal case;
wherein the first dorsal button and the second dorsal button are located where a side wall of the dorsal case meets an obverse face of the dorsal case;
wherein the first volar button and the second volar button are located on the volar case;
wherein the first volar button and the second volar button are located where a side wall of the volar case meets an obverse face of the volar case;
wherein the first dorsal button and the second dorsal button are positioned at a corner of the dorsal case for improved accessibility;
wherein the first volar button and the second volar button are positioned at a corner of the volar case for improved accessibility.

2. The tactical watch according to claim 1
wherein the dorsal case is coupled to the band and is adapted to be worn on the dorsal side of the wrist.

3. The tactical watch according to claim 2
wherein the volar case is coupled to the band and is adapted to be worn on the volar side of the wrist.

4. The tactical watch according to claim 3
wherein the dorsal case and the volar case each comprise the obverse face and a reverse face with the reverse face adapted to contact the wrist and the obverse face opposite the reverse face;
wherein the band is elastic such that the band stretches for donning and removing;
wherein the tactical watch comprises electrical connections between the dorsal case and the volar case that are hidden within the band;
wherein a plurality of buttons are adapted for a user to press in order to control features of the tactical watch.

5. The tactical watch according to claim 4
wherein the dorsal case, the volar case, or both comprise a rubberized coating to absorb mechanical shock incurred by dropping the tactical watch.

6. The tactical watch according to claim 4
wherein the dorsal case comprises the outward facing display located on the obverse face of the dorsal case and the volar case comprises the inward facing display located on the obverse face of the volar case.

7. The tactical watch according to claim 6
wherein the plurality of buttons are all located on the same side of the tactical watch;
wherein one or more sensors are adapted to monitor the user and/or the environment surrounding the tactical watch.

8. The tactical watch according to claim 7 wherein the plurality of buttons comprise at least one button designated as an UP button for navigating menus presented on the outward facing display, the inward facing display, or both;

wherein the plurality of buttons comprise at least one button designated as a DOWN button for navigating menus presented on the outward facing display, the inward facing display, or both;

wherein the plurality of buttons comprise at least one button designated as a SELECT/ENTER button for making selections from menus presented on the outward facing display, the inward facing display, or both.

9. The tactical watch according to claim 8 wherein the one or more sensors comprise a biometric contact sensor;

wherein the biometric contact sensor is located on the reverse face of the dorsal case, on the reverse face of the volar case, or both;

wherein the biometric contact sensor is adapted to contact the wrist;

wherein the biometric contact sensor measures body temperature, pulse rate, blood oxygen level, blood pressure, or any combination thereof.

10. The tactical watch according to claim 9 wherein the one or more sensors comprise a motion sensor;

wherein the motion sensor is located within the dorsal case, within the volar case, or both;

wherein the motion sensor measures acceleration of the tactical watch within three-dimensional space.

11. The tactical watch according to claim 10 wherein the motion sensor utilizes one or more MEMS accelerometers.

12. The tactical watch according to claim 10 wherein the tactical watch comprises a GPS receiver for determining the geographical location of the tactical watch and the current time.

13. The tactical watch according to claim 12 wherein the outward facing display, the inward facing display, or both are touch sensitive such that the outward facing display and/or the inward facing display are adapted to accept input from the user.

14. The tactical watch according to claim 13 wherein a display comprises a black background and a backlight having reduced visibility.

15. The tactical watch according to claim 13 wherein the tactical watch is adapted to present any or all of the following to the user utilizing the outward facing display, the inward facing display, or both: a time and date, a GPS location comprising a longitude, a latitude, an elevation, or any combination thereof, a blood pressure measurement, a calories burned estimate, a body temperature measurement, and a pulse rate measurement.

16. The tactical watch according to claim 15 wherein the display presents one or more menus for changing settings of the tactical watch;

wherein navigation and selection of the settings are performed using touchscreen displays.

17. The tactical watch according to claim 16 wherein the tactical watch comprises a battery;

wherein the battery comprises one or more energy-storage devices;

wherein the battery is a source of electrical energy to operate the outward facing display, the inward facing display, the touchscreen displays, the backlight, the GPS receiver, and the one or more sensors;

wherein the battery is rechargeable and/or replaceable.

18. The tactical watch according to claim 17 wherein the dorsal case, the volar case, and the band are waterproof such that the tactical watch is unharmed by sweat or submersion in water.

* * * * *